US008202982B2

(12) United States Patent
Freier et al.

(10) Patent No.: US 8,202,982 B2
(45) Date of Patent: *Jun. 19, 2012

(54) METHODS OF OBTAINING ACTIVE ANTISENSE COMPOUNDS

(75) Inventors: Susan M. Freier, San Diego, CA (US); Olga Matveeva, Salt Lake City, UT (US); Alexander Tsodikov, Salt Lake City, UT (US); Michael C. Giddings, Salt Lake City, UT (US); Jacqueline R. Wyatt, Sundance, WY (US)

(73) Assignee: Isis Phramaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/557,358

(22) Filed: Sep. 10, 2009

(65) Prior Publication Data
US 2010/0113292 A1    May 6, 2010

Related U.S. Application Data

(63) Continuation of application No. 10/686,317, filed on Oct. 15, 2003, now Pat. No. 7,592,440, which is a continuation of application No. 09/568,165, filed on May 9, 2000, now abandoned.

(51) Int. Cl.
*C07H 21/00* (2006.01)
*C07H 21/04* (2006.01)
*A61K 31/70* (2006.01)

(52) U.S. Cl. .................... 536/25.3; 536/24.5; 514/44

(58) Field of Classification Search .................... None
See application file for complete search history.

(56) References Cited

U.S. PATENT DOCUMENTS

| | | | |
|---|---|---|---|
| 5,523,389 A | 6/1996 | Ecker et al. |
| 5,661,135 A | 8/1997 | Robinson |
| 5,756,710 A | 5/1998 | Stein et al. |
| 5,801,154 A | 9/1998 | Baracchini et al. |
| 5,885,970 A | 3/1999 | Bennett et al. |
| 5,948,902 A | 9/1999 | Honkanen et al. |
| 5,952,490 A | 9/1999 | Hanecak et al. |
| 6,066,625 A | 5/2000 | MacLeod et al. |
| 6,214,805 B1 | 4/2001 | Torrence et al. |

FOREIGN PATENT DOCUMENTS

| | | |
|---|---|---|
| WO | WO 94/08053 | 4/1994 |
| WO | WO 99/01139 | 1/1999 |
| WO | WO 00/61810 | 10/2000 |

OTHER PUBLICATIONS

Matthews et al., "Predicting oligonucleotide affinity to nucleic acid targets" RNA (1999) 5:1458-1469.
Patzel et al., "A theoretical approach to select effective antisense oligodeoxyribonucleotides at high statistical probability" Nucl. Acids Res. (1999) 27:4328-4334.
Smetsers et al., "Bias in Nucleotide Composition of Antisense Oligonucleotides" Antisense and Nucleic Acid Drug Development (1996) 6:63-67.
Stewart et al., "Reduction of Expression of the Multidrug Resistance Protein (MRP) in Human Tumor Cells by Antisense Phosphorothioate Oligonucleotides" Biochem. Pharmacol. (1996) 51:461-469.
Stull et al., "Predicting antisense oligonucleotide inhibitory efficacy: a computational approach using histograms and thermodynamic indicies" Nucl. Acids Res. (1992) 20:3501-3508.
Toon et al., "Bias in Nucleotide Composition of Antisense Oligonucleotides" Antisense Nucl. Acid Drug Dev. (1996) 6:63-67.
Tu et al., "Tetranucleotide GGGA Motif in Primary RNA Transcripts" J. Biol. Chem. (1998) 273:25125-25131.
Wyatt et al., "Oligonucleotides Containing the G-Quartet Sequence Motif" Appl. Antisense Ther. Restenosis (1999) 133-140.
Wyatt et al., "Combinatorially selected guanosine-quartet structure is a potent inhibitor of human immunodeficiency virus envelope-mediated cell fusion" PNAS (1994) 91:1356-1360.
Wyatt et al., "Kinetics of G-Quartet-Mediated Tetramer Formation" Biochemistry (1996) 35:8001-8008.
Supplementary European Search Report for application EP 01932881 dated Jun. 23, 2003.
International Search Report for application PCT/US01/14157 dated Aug. 7, 2001.

*Primary Examiner* — Tracy Vivlemore
(74) *Attorney, Agent, or Firm* — Knobbe, Martens, Olson & Bear LLP

(57) ABSTRACT

Methods for obtaining antisense oligonucleotides with activity against a desired target are provided. Methods of identifying oligonucleotide sequence motifs which are predictive of antisense oligonucleotide activity are provided, as are motifs identified according to this method. Methods of selecting effective antisense oligonucleotide sequences and effective antisense target sequences are provided, as are sequences selected according to these methods. In other methods of the invention, oligonucleotides are designed to hybridize to target sequences containing one or more activity-enhancing motifs. Antisense oligonucleotides designed according to these methods are also provided.

5 Claims, 3 Drawing Sheets

SEQUENCE LISTING

<160> NUMBER OF SEQ ID NOS: 65

<210> SEQ ID NO 1
<211> LENGTH: 4
<212> TYPE: DNA
<213> ORGANISM: Artificial Sequence

```
<220> FEATURE:
<223> OTHER INFORMATION: motif

<400> SEQUENCE: 1 ccac                                                                      4

<210> SEQ ID NO 2
<211> LENGTH: 3
<212> TYPE: DNA
<213> ORGANISM: Artificial Sequence
<220> FEATURE:
<223> OTHER INFORMATION: motif

<400> SEQUENCE: 2 cca                                                                       3

<210> SEQ ID NO 3
<211> LENGTH: 3
<212> TYPE: DNA
<213> ORGANISM: Artificial Sequence
<220> FEATURE:
<223> OTHER INFORMATION: motif

<400> SEQUENCE: 3 ccc                                                                       3

<210> SEQ ID NO 4
<211> LENGTH: 4
<212> TYPE: DNA
<213> ORGANISM: Artificial Sequence
<220> FEATURE:
<223> OTHER INFORMATION: motif

<400> SEQUENCE: 4 tccc                                                                      4

<210> SEQ ID NO 5
<211> LENGTH: 4
<212> TYPE: DNA
<213> ORGANISM: Artificial Sequence
<220> FEATURE:
<223> OTHER INFORMATION: motif

<400> SEQUENCE: 5 ccca                                                                      4

<210> SEQ ID NO 6
<211> LENGTH: 4
<212> TYPE: DNA
<213> ORGANISM: Artificial Sequence
<220> FEATURE:
<223> OTHER INFORMATION: motif

<400> SEQUENCE: 6 ccct                                                                      4

<210> SEQ ID NO 7
<211> LENGTH: 4
<212> TYPE: DNA
<213> ORGANISM: Artificial Sequence
<220> FEATURE:
<223> OTHER INFORMATION: motif

<400> SEQUENCE: 7 cccc                                                                      4
```

```
<210> SEQ ID NO 8
<211> LENGTH: 4
<212> TYPE: DNA
<213> ORGANISM: Artificial Sequence
<220> FEATURE:
<223> OTHER INFORMATION: motif

<400> SEQUENCE: 8 actc                                                                   4

<210> SEQ ID NO 9
<211> LENGTH: 4
<212> TYPE: DNA
<213> ORGANISM: Artificial Sequence
<220> FEATURE:
<223> OTHER INFORMATION: motif

<400> SEQUENCE: 9 atcc                                                                   4

<210> SEQ ID NO 10
<211> LENGTH: 4
<212> TYPE: DNA
<213> ORGANISM: Artificial Sequence
<220> FEATURE:
<223> OTHER INFORMATION: motif

<400> SEQUENCE: 10 cacc                                                                   4

<210> SEQ ID NO 11
<211> LENGTH: 4
<212> TYPE: DNA
<213> ORGANISM: Artificial Sequence
<220> FEATURE:
<223> OTHER INFORMATION: motif

<400> SEQUENCE: 11 gcca                                                                   4

<210> SEQ ID NO 12
<211> LENGTH: 3
<212> TYPE: DNA
<213> ORGANISM: Artificial Sequence
<220> FEATURE:
<223> OTHER INFORMATION: motif

<400> SEQUENCE: 12 atc                                                                    3

<210> SEQ ID NO 13
<211> LENGTH: 3
<212> TYPE: DNA
<213> ORGANISM: Artificial Sequence
<220> FEATURE:
<223> OTHER INFORMATION: motif

<400> SEQUENCE: 13 cac                                                                    3

<210> SEQ ID NO 14
<211> LENGTH: 3
<212> TYPE: DNA
<213> ORGANISM: Artificial Sequence
<220> FEATURE:
<223> OTHER INFORMATION: motif

<400> SEQUENCE: 14
```

```
ctc                                                                   3

<210> SEQ ID NO 15
<211> LENGTH: 4
<212> TYPE: DNA
<213> ORGANISM: Artificial Sequence
<220> FEATURE:
<223> OTHER INFORMATION: motif

<400> SEQUENCE: 15 gcat                                                                  4

<210> SEQ ID NO 16
<211> LENGTH: 4
<212> TYPE: DNA
<213> ORGANISM: Artificial Sequence
<220> FEATURE:
<223> OTHER INFORMATION: motif

<400> SEQUENCE: 16 acca                                                                  4

<210> SEQ ID NO 17
<211> LENGTH: 4
<212> TYPE: DNA
<213> ORGANISM: Artificial Sequence
<220> FEATURE:
<223> OTHER INFORMATION: motif

<400> SEQUENCE: 17 catc                                                                  4

<210> SEQ ID NO 18
<211> LENGTH: 3
<212> TYPE: DNA
<213> ORGANISM: Artificial Sequence
<220> FEATURE:
<223> OTHER INFORMATION: motif

<400> SEQUENCE: 18 tcc                                                                   3

<210> SEQ ID NO 19
<211> LENGTH: 3
<212> TYPE: DNA
<213> ORGANISM: Artificial Sequence
<220> FEATURE:
<223> OTHER INFORMATION: motif

<400> SEQUENCE: 19 acc                                                                   3

<210> SEQ ID NO 20
<211> LENGTH: 4
<212> TYPE: DNA
<213> ORGANISM: Artificial Sequence
<220> FEATURE:
<223> OTHER INFORMATION: motif

<400> SEQUENCE: 20 ctct                                                                  4

<210> SEQ ID NO 21
<211> LENGTH: 4
<212> TYPE: DNA
<213> ORGANISM: Artificial Sequence
```

```
<220> FEATURE:
<223> OTHER INFORMATION: motif

<400> SEQUENCE: 21 gggg                                                                    4

<210> SEQ ID NO 22
<211> LENGTH: 3
<212> TYPE: DNA
<213> ORGANISM: Artificial Sequence
<220> FEATURE:
<223> OTHER INFORMATION: motif

<400> SEQUENCE: 22 ggg                                                                     3

<210> SEQ ID NO 23
<211> LENGTH: 3
<212> TYPE: DNA
<213> ORGANISM: Artificial Sequence
<220> FEATURE:
<223> OTHER INFORMATION: motif

<400> SEQUENCE: 23 taa                                                                     3

<210> SEQ ID NO 24
<211> LENGTH: 4
<212> TYPE: DNA
<213> ORGANISM: Artificial Sequence
<220> FEATURE:
<223> OTHER INFORMATION: motif

<400> SEQUENCE: 24 ggct                                                                    4

<210> SEQ ID NO 25
<211> LENGTH: 4
<212> TYPE: DNA
<213> ORGANISM: Artificial Sequence
<220> FEATURE:
<223> OTHER INFORMATION: motif

<400> SEQUENCE: 25 taaa                                                                    4

<210> SEQ ID NO 26
<211> LENGTH: 4
<212> TYPE: DNA
<213> ORGANISM: Artificial Sequence
<220> FEATURE:
<223> OTHER INFORMATION: motif

<400> SEQUENCE: 26 actg                                                                    4

<210> SEQ ID NO 27
<211> LENGTH: 4
<212> TYPE: DNA
<213> ORGANISM: Artificial Sequence
<220> FEATURE:
<223> OTHER INFORMATION: motif

<400> SEQUENCE: 27 gaaa                                                                    4
```

```
<210> SEQ ID NO 28
<211> LENGTH: 4
<212> TYPE: DNA
<213> ORGANISM: Artificial Sequence
<220> FEATURE:
<223> OTHER INFORMATION: motif

<400> SEQUENCE: 28 tggg                                                                        4

<210> SEQ ID NO 29
<211> LENGTH: 4
<212> TYPE: DNA
<213> ORGANISM: Artificial Sequence
<220> FEATURE:
<223> OTHER INFORMATION: motif

<400> SEQUENCE: 29 aaat                                                                        4

<210> SEQ ID NO 30
<211> LENGTH: 3
<212> TYPE: DNA
<213> ORGANISM: Artificial Sequence
<220> FEATURE:
<223> OTHER INFORMATION: motif

<400> SEQUENCE: 30 gga                                                                         3

<210> SEQ ID NO 31
<211> LENGTH: 4
<212> TYPE: DNA
<213> ORGANISM: Artificial Sequence
<220> FEATURE:
<223> OTHER INFORMATION: motif

<400> SEQUENCE: 31 ctgg                                                                        4

<210> SEQ ID NO 32
<211> LENGTH: 4
<212> TYPE: DNA
<213> ORGANISM: Artificial Sequence
<220> FEATURE:
<223> OTHER INFORMATION: motif

<400> SEQUENCE: 32 ataa                                                                        4

<210> SEQ ID NO 33
<211> LENGTH: 4
<212> TYPE: DNA
<213> ORGANISM: Artificial Sequence
<220> FEATURE:
<223> OTHER INFORMATION: motif

<400> SEQUENCE: 33 aata                                                                        4

<210> SEQ ID NO 34
<211> LENGTH: 4
<212> TYPE: DNA
<213> ORGANISM: Artificial Sequence
<220> FEATURE:
<223> OTHER INFORMATION: motif

<400> SEQUENCE: 34
```

```
ccgg                                                                4

<210> SEQ ID NO 35
<211> LENGTH: 3
<212> TYPE: DNA
<213> ORGANISM: Artificial Sequence
<220> FEATURE:
<223> OTHER INFORMATION: motif

<400> SEQUENCE: 35 ata                                                                 3

<210> SEQ ID NO 36
<211> LENGTH: 3
<212> TYPE: DNA
<213> ORGANISM: Artificial Sequence
<220> FEATURE:
<223> OTHER INFORMATION: motif

<400> SEQUENCE: 36 aaa                                                                 3

<210> SEQ ID NO 37
<211> LENGTH: 4
<212> TYPE: DNA
<213> ORGANISM: Artificial Sequence
<220> FEATURE:
<223> OTHER INFORMATION: motif

<400> SEQUENCE: 37 ggag                                                                4

<210> SEQ ID NO 38
<211> LENGTH: 3
<212> TYPE: DNA
<213> ORGANISM: Artificial Sequence
<220> FEATURE:
<223> OTHER INFORMATION: motif

<400> SEQUENCE: 38 ctg                                                                 3

<210> SEQ ID NO 39
<211> LENGTH: 4
<212> TYPE: DNA
<213> ORGANISM: Artificial Sequence
<220> FEATURE:
<223> OTHER INFORMATION: motif

<400> SEQUENCE: 39 gtgg                                                                4

<210> SEQ ID NO 40
<211> LENGTH: 3
<212> TYPE: DNA
<213> ORGANISM: Artificial Sequence
<220> FEATURE:
<223> OTHER INFORMATION: motif

<400> SEQUENCE: 40 tgg                                                                 3

<210> SEQ ID NO 41
<211> LENGTH: 4
<212> TYPE: DNA
<213> ORGANISM: Artificial Sequence
```

```
<220> FEATURE:
<223> OTHER INFORMATION: motif

<400> SEQUENCE: 41 ggga                                                                4

<210> SEQ ID NO 42
<211> LENGTH: 4
<212> TYPE: DNA
<213> ORGANISM: Artificial Sequence
<220> FEATURE:
<223> OTHER INFORMATION: motif

<400> SEQUENCE: 42 aggg                                                                4

<210> SEQ ID NO 43
<211> LENGTH: 4
<212> TYPE: DNA
<213> ORGANISM: Artificial Sequence
<220> FEATURE:
<223> OTHER INFORMATION: motif

<400> SEQUENCE: 43 gagt                                                                4

<210> SEQ ID NO 44
<211> LENGTH: 4
<212> TYPE: DNA
<213> ORGANISM: Artificial Sequence
<220> FEATURE:
<223> OTHER INFORMATION: motif

<400> SEQUENCE: 44 ggat                                                                4

<210> SEQ ID NO 45
<211> LENGTH: 4
<212> TYPE: DNA
<213> ORGANISM: Artificial Sequence
<220> FEATURE:
<223> OTHER INFORMATION: motif

<400> SEQUENCE: 45 ggtg                                                                4

<210> SEQ ID NO 46
<211> LENGTH: 4
<212> TYPE: DNA
<213> ORGANISM: Artificial Sequence
<220> FEATURE:
<223> OTHER INFORMATION: motif

<400> SEQUENCE: 46 tggc                                                                4

<210> SEQ ID NO 47
<211> LENGTH: 3
<212> TYPE: DNA
<213> ORGANISM: Artificial Sequence
<220> FEATURE:
<223> OTHER INFORMATION: motif

<400> SEQUENCE: 47 gat                                                                 3
```

```
<210> SEQ ID NO 48
<211> LENGTH: 3
<212> TYPE: DNA
<213> ORGANISM: Artificial Sequence
<220> FEATURE:
<223> OTHER INFORMATION: motif

<400> SEQUENCE: 48 gtg                                                                3

<210> SEQ ID NO 49
<211> LENGTH: 3
<212> TYPE: DNA
<213> ORGANISM: Artificial Sequence
<220> FEATURE:
<223> OTHER INFORMATION: motif

<400> SEQUENCE: 49 gag                                                                3

<210> SEQ ID NO 50
<211> LENGTH: 4
<212> TYPE: DNA
<213> ORGANISM: Artificial Sequence
<220> FEATURE:
<223> OTHER INFORMATION: motif

<400> SEQUENCE: 50 atgc                                                               4

<210> SEQ ID NO 51
<211> LENGTH: 4
<212> TYPE: DNA
<213> ORGANISM: Artificial Sequence
<220> FEATURE:
<223> OTHER INFORMATION: motif

<400> SEQUENCE: 51 tggt                                                               4

<210> SEQ ID NO 52
<211> LENGTH: 4
<212> TYPE: DNA
<213> ORGANISM: Artificial Sequence
<220> FEATURE:
<223> OTHER INFORMATION: motif

<400> SEQUENCE: 52 gatg                                                               4

<210> SEQ ID NO 53
<211> LENGTH: 3
<212> TYPE: DNA
<213> ORGANISM: Artificial Sequence
<220> FEATURE:
<223> OTHER INFORMATION: motif

<400> SEQUENCE: 53 ggt                                                                3

<210> SEQ ID NO 54
<211> LENGTH: 4
<212> TYPE: DNA
<213> ORGANISM: Artificial Sequence
<220> FEATURE:
<223> OTHER INFORMATION: motif

<400> SEQUENCE: 54
```

```
agag                                                4

<210> SEQ ID NO 55
<211> LENGTH: 4
<212> TYPE: DNA
<213> ORGANISM: Artificial Sequence
<220> FEATURE:
<223> OTHER INFORMATION: motif

<400> SEQUENCE: 55 agcc                                                4

<210> SEQ ID NO 56
<211> LENGTH: 4
<212> TYPE: DNA
<213> ORGANISM: Artificial Sequence
<220> FEATURE:
<223> OTHER INFORMATION: motif

<400> SEQUENCE: 56 ttta                                                4

<210> SEQ ID NO 57
<211> LENGTH: 4
<212> TYPE: DNA
<213> ORGANISM: Artificial Sequence
<220> FEATURE:
<223> OTHER INFORMATION: motif

<400> SEQUENCE: 57 cagt                                                4

<210> SEQ ID NO 58
<211> LENGTH: 4
<212> TYPE: DNA
<213> ORGANISM: Artificial Sequence
<220> FEATURE:
<223> OTHER INFORMATION: motif

<400> SEQUENCE: 58 tttc                                                4

<210> SEQ ID NO 59
<211> LENGTH: 4
<212> TYPE: DNA
<213> ORGANISM: Artificial Sequence
<220> FEATURE:
<223> OTHER INFORMATION: motif

<400> SEQUENCE: 59 attt                                                4

<210> SEQ ID NO 60
<211> LENGTH: 4
<212> TYPE: DNA
<213> ORGANISM: Artificial Sequence
<220> FEATURE:
<223> OTHER INFORMATION: motif

<400> SEQUENCE: 60 ccag                                                4

<210> SEQ ID NO 61
<211> LENGTH: 4
<212> TYPE: DNA
<213> ORGANISM: Artificial Sequence
```

```
<220> FEATURE:
<223> OTHER INFORMATION: motif

<400> SEQUENCE: 61 ttat                                                                    4

<210> SEQ ID NO 62
<211> LENGTH: 4
<212> TYPE: DNA
<213> ORGANISM: Artificial Sequence
<220> FEATURE:
<223> OTHER INFORMATION: motif

<400> SEQUENCE: 62 tatt                                                                    4

<210> SEQ ID NO 63
<211> LENGTH: 3
<212> TYPE: DNA
<213> ORGANISM: Artificial Sequence
<220> FEATURE:
<223> OTHER INFORMATION: motif

<400> SEQUENCE: 63 tat                                                                     3

<210> SEQ ID NO 64
<211> LENGTH: 4
<212> TYPE: DNA
<213> ORGANISM: Artificial Sequence
<220> FEATURE:
<223> OTHER INFORMATION: motif

<400> SEQUENCE: 64 ctcc                                                                    4

<210> SEQ ID NO 65
<211> LENGTH: 3
<212> TYPE: DNA
<213> ORGANISM: Artificial Sequence
<220> FEATURE:
<223> OTHER INFORMATION: motif

<400> SEQUENCE: 65 cag                                                                     3
```

US 8,202,982 B2

METHODS OF OBTAINING ACTIVE ANTISENSE COMPOUNDS

CROSS-REFERENCE TO RELATED APPLICATIONS

The present application is a continuation of U.S. patent application Ser. No. 10/686,317 filed Oct. 15, 2003, now allowed as U.S. Pat. No. 7,295,440 to be issued Sep. 22, 2009, which is a continuation of U.S. patent application Ser. No. 09/568,165 filed May 9, 2000, now abandoned, each of which are incorporated herein by reference in its entirety.

This invention was made, in part, with funding under NIH Grant Nos. 5RO1-GM48152-07 and 2P30 CA42014-12 and DOE grant No. DE-FG03-99ER62732. The U.S. Government has certain rights in this invention.

SEQUENCE LISTING

The present application is being filed along with a Sequence Listing in electronic format. The Sequence Listing is provided as a file entitled ISPH0794USC1SEQ.txt, created on Sep. 9, 2009 which is 12 Kb in size. The information in the electronic format of the sequence listing is incorporated herein by reference in its entirety.

FIELD OF THE INVENTION

The present invention relates to methods of obtaining effective antisense compounds. Antisense compounds are widely used in therapeutics, diagnostics and as research tools, such as in target validation. The present invention provides methods of identifying oligonucleotide sequence motifs which are predictive of antisense activity. Methods for selecting effective antisense oligonucleotide sequences for inhibition of expression of a target nucleic acid are provided, as are methods for selecting effective antisense target sequences. Methods of designing antisense compounds are also provided.

BACKGROUND OF THE INVENTION

An important step in antisense technology is identification of mRNA sites that can be targeted efficiently. Many experiments have shown that certain antisense oligonucleotides are more efficient than others in suppressing specific gene expression. A routine approach to finding the most active antisense oligonucleotides involves the synthesis of numerous oligonucleotides, (often up to several dozen) complementary to different regions of the targeted mRNA, followed by activity screening of the oligonucleotides in cells. Alahari, S. K. et al., *Mol. Pharmacol.*, 1996, 50, 808-19; Bennett, C. F., Condon, T. P., Grimm, S., Chan, H. & Chiang, M. Y., *J. Immunol.*, 1994, 152, 3530-40; Chiang, M. Y. et al., *J. Biol. Chem.*, 1991, 266, 18162-71; Dean, N. M., McKay, R., Condon, T. P. & Bennett, C. F., *J. Biol. Chem.*, 1994, 269, 16416-24; Dean, N. M. et al., *Biochem. Soc. Trans.*, 1996, 24, 623-9; Duff, J. L., Monia, B. P. & Berk, B. C., *J. Biol. Chem.*, 1995, 270, 7161-6; Lee, C. H. et al., *Shock*, 1995, 4, 1-10; Lefebvre d'Hellencourt, C., Diaw, L., Cornillet, P. & Guenounou, M., *Biochim. Biophys. Acta*, 1996, 1317, 168-74; Miraglia, L., Geiger, T., Bennett, C. F. & Dean, N. M., *Int. J. Immunopharmacol.*, 1996, 18, 227-40; Stepkowski, S. M., Tu, Y., Condon, T. P. & Bennett, C. F., *J. Immunol.*, 1994, 153, 5336-46; *J. Immunol.*, 1995 154, 1521; Stewart, A. J. et al., *Biochem. Pharmacol.*, 1996, 51, 461-9. Strategies for increasing the percentage of active antisense oligonucleotides should have significant benefit. A variety of such strategies have been tried, using a range of criteria of oligonucleotide design.

The calculated Gibbs free energy ($\Delta G$) values for duplex formation between an oligonucleotide and mRNA molecule correlates with oligonucleotide antisense activity (Stewart, A. J. et al., *Biochem. Pharmacol.*, 1996, 51, 461-469), though hybridization affinity alone is not sufficient to ensure antisense oligonucleotide efficiency in cells. Chiang et al., *J. Biol. Chem.*, 1991, 266, 18162-18171. Systematic alignment of computer-predicted local RNA secondary structures has also been attempted in selecting antisense oligonucleotides for inhibition of intracellular adhesion molecule-1 (ICAM-1) expression. Patzel et al., *Nucl. Acids Res.*, 1999, 27, 4328-4334. The predicted stabilities of antisense oligonucleotide: target-RNA duplexes and their competition with predicted secondary structures of both the targets and antisense oligonucleotides have also been studied as a means to predict antisense efficacy. Stull et al., *Nucl. Acids Res.*, 1992, 20, 3501-3508; Mathews et al., *RNA*, 1999, 5, 1458-1469. In spite of these proposed methods, however, active antisense compounds are still generally identified through empirical testing of multiple antisense sequences.

Sequence-based strategies for predicting antisense efficacy have also been tried. Smetsers et al. have found that there is a bias in the nucleotide composition of active antisense oligonucleotides, with GG, CCC, CC, GAC and CG motifs significantly overrepresented and TT and TCC significantly underrepresented in a database of 206 antisense oligonucleotides from the published literature (G, C, A and T represent the four major DNA nucleobases guanine, cytosine, adenine and thymine, and/or their corresponding nucleosides guanosine, cytidine, adenosine and thymidine). However, some of these motifs are reported in the literature to induce nonantisense effects such as by protein binding or mitogenic mechanisms. The authors conclude that further analysis is needed to investigate whether these motifs should be avoided or favored in oligonucleotide design. Smetsers et al., *Antisense Nucl. Acid Drug Dev.*, 1996, 6, 63-67.

While Smetsers found that CCC is overrepresented and TCC is underrepresented among active antisense sequences, Tu et al. found that the TCCC motif is overrepresented among the most active oligonucleotides compared to their inactive counterparts. Tu, G. et al., *J. Biol. Chem.*, 1998, 273, 25125-25131 and WO 99/01139. In an analysis of published oligonucleotide sequences and in prospective experiments with TNF-α mRNA, oligonucleotides containing the TCCC motif were found to have a much higher success rate (50%) than oligonucleotides selected by trial and error (6%). Tu, G. et al., *J. Biol. Chem.*, 1998, 273, 25125-25131. Antisense oligonucleotides for inhibiting TNF" which comprise a TCCC motif are claimed. Methods of making antisense oligonucleotides which target a sequence comprising a GGGA motif and methods of inhibiting gene expression with these oligonucleotides are also disclosed and claimed. Methods of predicting the efficacy of an antisense oligonucleotide by determining whether the oligonucleotide is complementary to an RNA sequence containing a GGGA motif are also claimed. WO 99/01139.

Non-antisense biological effects have been observed when cells are treated with phosphorothioate oligonucleotides containing four contiguous guanosines. These oligonucleotides were demonstrated to form tetrameric (four-stranded) structures. Non-antisense effects have also been observed with phosphorothioate and phosphodiester oligonucleotides that contain several sets of consecutive guanosines. The G-quartet structure has been implicated in oligonucleotide binding to proteins. Wyatt, J. R. and Stein, C. A., *Appl. Antisense Ther.*

Restenosis, 1999, pp. 133-140. Kluwer, Boston, Mass. Oligonucleotides containing the sequence GGGG ($G_4$) have been found to have antiviral activity against a number of viruses.

Sequences containing a $G_4$ motif or two or more $G_3$ motifs has been found to be effective antivirals. It has also been reported that oligonucleotides containing a conserved $G_4$ core sequence or two stretches of 3 G's are effective inhibitors of phospholipase $A_2$ activity and that such oligonucleotides could be useful for modulation of telomere length on chromosomes. Wyatt et al., *Proc. Natl. Acad. Sci. U.S.A.*, 1994, 91, 1356-1360; Wyatt et al., *Biochemistry*, 1996, 35, 8002-8008; U.S. Pat. Nos. 5,523,389, 5,756,710 and 5,952,490; WO 94/08053.

According to the present invention, a series of oligonucleotide sequence motifs have been identified which, when present in an antisense oligonucleotide, have been demonstrated to be either positively or negatively correlated with antisense activity of the oligonucleotide. Consequently, a series of target sequence motifs complementary to the oligonucleotide sequence motifs have correspondingly been demonstrated to be either positively or negatively correlated with antisense activity when an oligonucleotide is targeted to a nucleic acid sequence containing such target sequence motifs. Several dozens of such motifs have been identified. Compositions and methods using these motifs are herein provided.

SUMMARY OF THE INVENTION

The present invention provides methods of identifying oligonucleotide sequence motifs which are correlated with, or which are predictive of, antisense oligonucleotide activity, and motifs identified according to these methods.

Also provided are methods of selecting effective antisense oligonucleotide sequences for inhibition of expression of a preselected target nucleic acid, according to which methods a set of antisense oligonucleotide sequences of desired length are provided which are complementary to the preselected target nucleic acid sequence. From this set are selected the antisense oligonucleotide sequences which contain at least one activity-enhancing oligonucleotide sequence motif. Preferably these antisense oligonucleotide sequences do not contain an activity-decreasing oligonucleotide sequence motif. Also preferably, these antisense oligonucleotide sequences contain more than one activity-enhancing oligonucleotide sequence motif. Antisense oligonucleotide sequences selected according to these methods are also provided.

Further provided are methods of selecting effective antisense target sequences for inhibition of expression of a preselected target nucleic acid, according to which methods the target nucleic acid sequence is divided into a set of target sequence regions of desired length for antisense targeting. From this set are selected the target sequence regions which contain at least one activity-enhancing target sequence motif. Preferably these target sequence regions do not contain an activity-decreasing target sequence motif. Also preferably, these target sequence regions contain more than one activity-enhancing target sequence motif. Antisense target sequences selected according to these methods are also provided.

The present invention also provides methods for designing antisense oligonucleotides with enhanced likelihood of inhibiting expression of a preselected nucleic acid target compared to antisense oligonucleotides designed at random. Oligonucleotides are targeted to nucleic acid target sequences which contain at least one activity-enhancing target sequence motif. Preferably, two or more activity-enhancing target sequence motifs are present in the target sequence. Preferably, no activity-decreasing target sequence motifs are present in the target sequence. In another embodiment, oligonucleotides are targeted to nucleic acid target sequences which do not contain any activity-decreasing target sequence motifs. Preferably, at least one activity-enhancing target sequence motifs is also present in the target sequence. Antisense oligonucleotides made according to these methods are also provided.

DETAILED DESCRIPTION OF THE INVENTION

Figure 1:
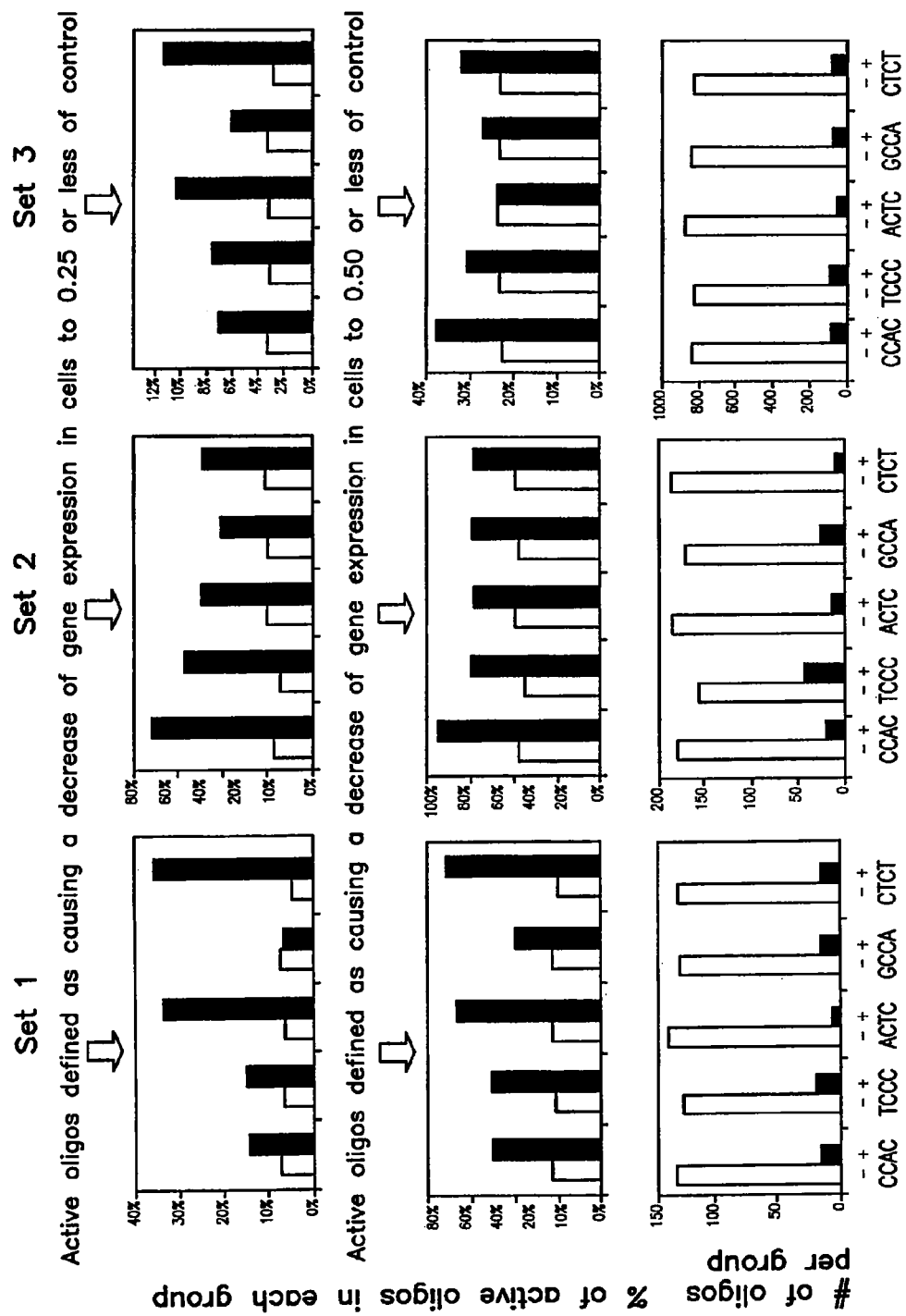
FIG. 1 is a series of bar graphs showing a positive correlation of antisense oligonucleotide activity with the presence of certain sequence motifs (CCAC, TCCC, ACTC, GCCA, CTCT; SEQ ID NO: 1, 4, 8, 11 and 20, respectively). Oligonucleotides from the database were categorized into groups according to the presence or absence of these "positive" motifs the presence of which correlates with antisense activity. The white bars represent groups of oligonucleotides without these motifs. The black bars represent groups of oligonucleotides with positive motifs. Sets 1, 2 and 3 are described hereinbelow. The top row of graph panels shows active oligonucleotides, defined as causing at least 75% reduction in target protein or mRNA expression. The middle row of graph panels shows active oligonucleotides, defined as causing at least 50% reduction in target protein or mRNA expression. The bottom row of graph panels shows the number of oligonucleotides per group.
Figure 2:
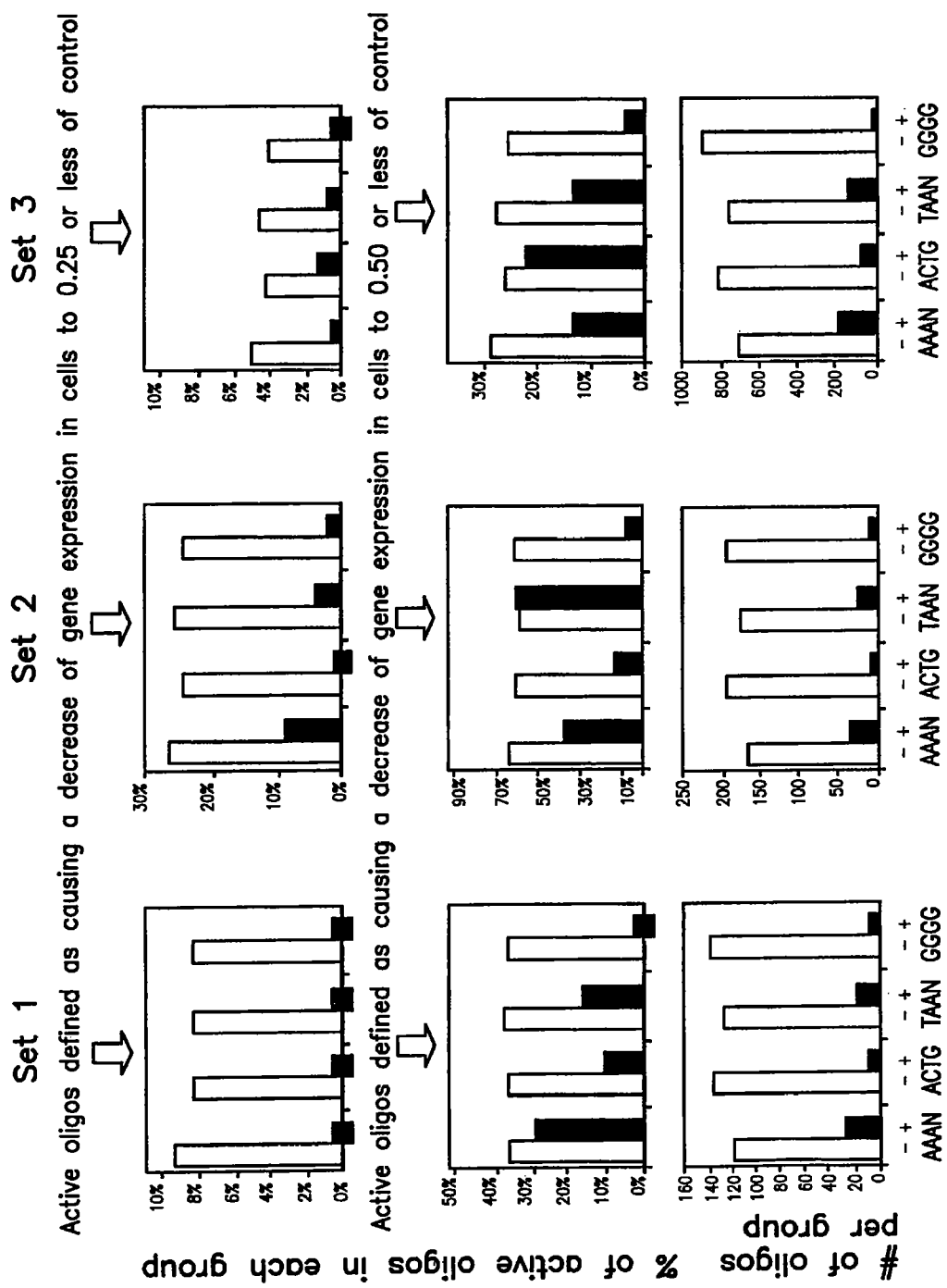
FIG. 2 is a series of bar graphs showing a negative correlation of antisense oligonucleotide activity with the presence of certain sequence motifs (AAA, ACTG, TAA, GGGG; SEQ ID NO: 36, 26, 23 and 21, respectively). Oligonucleotides from the database were categorized into groups according to the presence or absence of these "negative" motifs the absence of which correlates with antisense activity. The white bars represent groups of oligonucleotides without these motifs. The black bars represent groups of oligonucleotides with negative motifs. Sets 1, 2 and 3 are described hereinbelow. The top row of graph panels shows active oligonucleotides, defined as causing at least 75% reduction in target protein or mRNA expression. The middle row of graph panels shows active oligonucleotides, defined as causing at least 50% reduction in target protein or mRNA expression. The bottom row of graph panels shows the number of oligonucleotides per group.

Methods are described herein for obtaining antisense compounds with an enhanced likelihood of activity, i.e., an enhanced likelihood of inhibiting expression of a preselected target nucleic acid. This means that for a given number of antisense oligonucleotides designed and screened, a higher percentage will be active using this method to design oligonucleotides than if the antisense oligonucleotides were designed randomly. Conversely, fewer oligonucleotides have to be designed and screened to find a given number of active oligonucleotide compounds. Antisense compounds specifically hybridize with one or more nucleic acids encoding a preselected target. As used herein, the terms "target nucleic acid" and "nucleic acid encoding the target" encompass DNA encoding the target, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of the target. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense inhibition. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding the target. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding the target, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

All of the above-described regions are available for antisense targeting. According to the present invention, target regions are chosen which contain one or more "activity-enhancing target sequence motifs," also known as "positive predictor target sequence motifs," or "positive target motifs" which are sequence motifs in the target sequence, possibly as short as two nucleotides but preferably three or four nucleotides in length and possibly longer, the presence of which has been demonstrated to be positively correlated with activity of an antisense oligonucleotide targeted to that site. This correlation was demonstrated by statistical analysis of numerous antisense oligonucleotides, as described hereinbelow. Target regions which contain two or more activity-enhancing motifs are preferred. Activity-enhancing target sequence motifs which have been identified in accordance with the present invention include 5'-GTGG-3', 5'-TGG-3', 5'-GGG-3', 5'-GGGA-3', 5'-TGGG-3', 5'-AGGG-3', 5'-GGGG-3', 5'-GAGT-3', 5'-GGAT-3', 5'-GGTG-3', 5'-TGGC-3', 5'-GAT-3', 5'-GTG-3', 5'-GAG-3', 5'-ATGC-3', 5'-TGGT-3', 5'-GATG-3', 5'-GGA-3', 5'-GGT-3' and 5'-AGAG-3' in the target nucleic acid, which correspond to 5'-CCAC-3', 5'-CCA-3', 5'-CCC-3', 5'-TCCC-3', 5'-CCCA-3', 5'-CCCT-3', 5'-CCCC-3', 5'-ACTC-3', 5'-ATCC-3', 5'-CACC-3', 5'-GCCA-3' 5'-ATC-3', 5'-CAC-3', 5'-CTC-3', 5'-GCAT-3', 5'-ACCA-3', 5'-CATC-3', 5'-TCC-3', 5'-ACC-3' and 5'-CTCT-3' in the complementary antisense oligonucleotide(s). These motifs are preferably included when designing antisense oligonucleotides (i.e., when choosing target sequences).

Target sequence motifs have also been identified, as a result of this same statistical analysis, which are negatively correlated with activity of antisense oligonucleotides targeted to that sequence motif. These "activity-decreasing target sequence motifs" or "negative predictor target sequence motifs" (or simply "negative target motifs") are sequence motifs in the target sequence, possibly as short as two nucleotides but preferably three or four nucleotides in length and possibly longer, the presence of which has been demonstrated to be negatively correlated with activity of an antisense oligonucleotide targeted to that site. Activity-decreasing target sequence motifs which have been identified in accordance with the present invention include 5'-CCCC-3', 5'-CCC-3', 5'-AGCC-3', 5'-TTTA-3', 5'-CAGT-3', 5'-TTTC-3', 5'-CCCA-3', 5'-ATTT-3', 5'-TCC-3', 5'-CCAG-3', 5'-TTAT-3', 5'-TATT-3', 5'-CCGG-3', 5'-TAT-3', 5'-CTCC-3', 5'-CAG-3', 5'-TTT-3' and 5'-TTA-3' in the target nucleic acid, which correspond to 5'-GGGG-3', 5'-GGG-3', 5'-GGCT-3', 5'-TAAA-3', 5'-ACTG-3', 5'-GAAA-3', 5'-TGGG-3', 5'-AAAT-3', 5'-GGA-3', 5'-CTGG-3', 5'-ATAA-3', 5'-AATA-3', 5'-CCGG-3', 5'-ATA-3', 5'-GGAG-3', 5'-CTG-3', 5'-AAA-3' and 5'-TAA-3' in the complementary antisense oligonucleotide(s). These motifs are preferably avoided when designing antisense oligonucleotides (i.e., when choosing target sequences).

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

The activity-enhancing motifs and activity-decreasing motifs described herein were determined by statistical analysis of a database compiled from published data on active antisense oligonucleotides. This database facilitates analysis of oligonucleotides for correlation of activity and sequence motif, because the database can be queried by activity (in order to look at sequence motifs contained in active oligonucleotides) or by sequence (in order to look at activity of a given sequence motif), to give two examples. Manual analyses and correlations are, of course, also possible. Two selection criteria were used for choosing publications from which to extract oligonucleotide sequences for inclusion in the database. First, activity of oligonucleotides must have been measured by assays that evaluated the cellular level of antisense effect on a specific mRNA or its protein product. Second, at least ten different oligonucleotides targeted to the same mRNA had to have been tested under identical experimental conditions. The resulting database contains the names of targeted nucleic acids (genes or mRNAs), oligonucleotide sequences, data on their antisense activities (expressed as ratio of levels of target product vs control, measured in cells after treatment with experimental antisense vs. control oligonucleotide), and literature references. The database is updated on an ongoing basis and is available at http://antisense/genetics/utah.edu. Unlike previous work of this kind, this database includes data from oligonucleotides that target different parts of mRNA rather than molecules that are complementary only to mRNA translation initiation regions. This approach permits independence from any motif bias related to initiation sequences.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the methods of the present invention comprehend methods of designing other oligomeric antisense compounds, including but not limited to oligonucleotide mimetics such as are described below. The antisense compounds preferably comprise from about 8 to about 30 nucleobases (i.e. from about 8 to about 30 linked nucleosides). Particularly preferred antisense compounds are antisense oligonucleotides, even more preferably those comprising from about 12 to about 25 nucleobases. As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of antisense compounds include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497-1500.

Often preferred for antisense use are oligonucleotides with phosphorothioate backbones and oligonucleosides with heteroatom backbones, and in particular $—CH_2—NH—O—CH_2—$, $—CH_2—N(CH_3)—O—CH_2—$ [known as a methylene (methylimino) or MMI backbone], $—CH_2—O—N(CH_3)—CH_2—$, $—CH_2—N(CH_3)—N(CH_3)—CH_2—$ and $—O—N(CH_3)—CH_2—CH_2—$ [wherein the native phosphodiester backbone is represented as $—O—P—O—CH_2—$] of the above referenced U.S. Pat. No. 5,489,677, and the amide backbones of the above referenced U.S. Pat. No. 5,602,240. Also often used are oligonucleotides having morpholino backbone structures of the above-referenced U.S. Pat. No. 5,034,506.

Modified oligonucleotides may also contain one or more substituted sugar moieties. Such oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly useful are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other useful oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, poly-alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A very useful modification includes 2'-methoxyethoxy (2'-O—CH$_2$CH$_2$OCH$_3$, also known as 2'-O-(2-methoxyethyl) or 2'-MOE) (Martin et al., *Helv. Chim. Acta,* 1995, 78, 486-504) i.e., an alkoxyalkoxy group. Other modifications includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$, also described in examples hereinbelow.

Other modifications include 2'-methoxy (2'-O—CH$_3$), 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently believed to be useful base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, each of which is herein incorporated by reference, and U.S. Pat. No. 5,750,692, which is also herein incorporated by reference.

Other modifications of the oligonucleotides of the invention involve chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide.

Antisense compounds may be chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

Antisense compounds may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Antisense compounds encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 to Imbach et al.

Antisense compounds can be utilized for diagnostics, therapeutics, prophylaxis and as research reagents and kits. For therapeutics, an animal, preferably a human, suspected of having a disease or disorder which can be treated by modulating the expression of the target is treated by administering antisense compounds. The compounds can be utilized in pharmaceutical compositions by adding an effective amount of an antisense compound to a suitable pharmaceutically acceptable diluent or carrier. Use of the antisense compounds may also be useful prophylactically, e.g., to prevent or delay infection, inflammation or tumor formation, for example.

Antisense compounds are also useful for research and diagnostics, because these compounds hybridize to nucleic acids encoding the target, enabling sandwich and other assays to easily be constructed to exploit this fact. Hybridization of the antisense oligonucleotides with a nucleic acid encoding the target can be detected by means known in the art. Such means may include conjugation of an enzyme to the oligonucleotide, radiolabelling of the oligonucleotide or any other suitable detection means. Kits using such detection means for detecting the level of the target in a sample may also be prepared.

Antisense compounds are often included in pharmaceutical compositions and formulations. The pharmaceutical compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations may conveniently be presented in unit dosage form, and may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions may be formulated into any of many possible dosage forms such as, but not limited to, tablets, capsules, liquid syrups, soft gels, suppositories, and enemas. The compositions may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Subsets of Oligonucleotides that were Used for Statistical Analysis

To determine the extent and consistency of the effect of certain motifs in increasing, or decreasing, the proportion of active oligonucleotides, three sets of data were used. The first set (set 1) utilizes the oligonucleotides studied in the screening experiments published by Isis Pharmaceuticals, Inc. (147 oligonucleotides). The second set (set 2) utilizes experiments reported by other investigators under more heterogeneous conditions (202 oligonucleotides). The third set (set 3) utilizes the data from unpublished experiments performed by ISIS Pharmaceuticals (908 oligonucleotides). One important test of consistency was to analyze the data with two groupings of the active oligonucleotides. One group contains oligonucleotides that decrease the level of target mRNA or protein expression in cells to ≦50% of the control level (≧50% inhibition) and the other group, a subset of the first, contains oligonucleotides that decrease the level of mRNA, or protein, to ≦25% of control (≧75% inhibition).

Example 2

Determination of Correlation Coefficients for Motif Occurrence and Antisense Activity Each oligonucleotide sequence was subdivided into subsequences (motifs) which were either 3 or 4 nucleotides long. Correlation coefficients for motif occurrence and antisense oligonucleotide activity were determined with the combined data sets from published experiments (set 1 and set 2). This analysis revealed several dozen motifs with significant correlation coefficient values, either positive or negative, for antisense activity. Correlation analysis (T-test) was chosen rather than the chi-square test as it avoids defining an arbitrary cutoff point in classifying oligonucleotides as active or inactive by utilizing continuous activity input.

Example 3

Verification of Motifs Using "Minus One mRNA" Approach

To eliminate "false positive" motifs that were incorrectly identified as being correlated with antisense activity, e.g., identified based on potentially biased or inaccurate data, a "minus one mRNA" verification was used. In this procedure, oligonucleotide subsets that target a given mRNA were removed, in turn, from the database and the remaining parts of the database were analyzed to find motifs with significant correlation coefficients. Motifs whose activity was found to be unique to a particular mRNA target were then eliminated.

The remaining motifs are shown in Table 1 (oligonucleotide motifs positively correlated with antisense activity) and Table 2 (oligonucleotide motifs negatively correlated with antisense activity).

TABLE 1

Oligonucleotide motifs positively correlated with antisense activity

| Motif sequence | SEQ ID NO: | Correlation coefficient | Significance of correlation | Direction of effect |
| --- | --- | --- | --- | --- |
| CCAC | 1 | 0.31 | $2.62 \times 10^{-09}$ | positive |
| CCA | 2 | 0.30 | <0.005 | positive |
| CCC | 3 | 0.30 | <0.005 | positive |
| TCCC | 4 | 0.30 | $1.53 \times 10^{-08}$ | positive |
| CCCA | 5 | 0.27 | $4.69 \times 10^{-06}$ | positive |
| CCCT | 6 | 0.25 | 0.00005 | positive |
| CCCC | 7 | 0.24 | 0.00001 | positive |
| ACTC | 8 | 0.20 | 0.00018 | positive |
| ATCC | 9 | 0.20 | 0.00027 | positive |
| CACC | 10 | 0.19 | 0.00043 | positive |
| GCCA | 11 | 0.18 | 0.00065 | positive |
| ATC | 12 | 0.18 | 0.00091 | positive |
| CAC | 13 | 0.16 | 0.00246 | positive |
| CTC | 14 | 0.16 | 0.00348 | positive |
| GCAT | 15 | 0.15 | 0.0044 | positive |
| ACCA | 16 | 0.15 | 0.00499 | positive |
| CATC | 17 | 0.15 | 0.00513 | positive |
| TCC | 18 | 0.15 | 0.00539 | positive |

TABLE 1-continued

Oligonucleotide motifs positively correlated with antisense activity

| Motif sequence | SEQ ID NO: | Correlation coefficient | Significance of correlation | Direction of effect |
|---|---|---|---|---|
| ACC | 19 | 0.14 | 0.00862 | positive |
| CTCT | 20 | 0.14 | 0.00864 | positive |

TABLE 2

Oligonucleotide motifs negatively correlated with antisense activity

| Motif sequence | SEQ ID NO: | Correlation coefficient | Significance of correlation | Direction of effect |
|---|---|---|---|---|
| GGGG | 21 | −0.24 | 0.00001 | negative |
| GGG | 22 | −0.23 | 0.00001 | negative |
| TAA | 23 | −0.2 | 0.002 | negative |
| GGCT | 24 | −0.19 | 0.00037 | negative |
| TAAA | 25 | −0.18 | 0.00099 | negative |
| ACTG | 26 | −0.17 | 0.00224 | negative |
| GAAA | 27 | −0.16 | 0.00296 | negative |
| TGGG | 28 | −0.16 | 0.00298 | negative |
| AAAT | 29 | −0.16 | 0.00342 | negative |
| GGA | 30 | −0.15 | 0.00396 | negative |
| CTGG | 31 | −0.14 | 0.00797 | negative |
| ATAA | 32 | −0.14 | 0.00951 | negative |
| AATA | 33 | −0.12 | 0.02666 | negative |
| CCGG | 34 | −0.12 | 0.03227 | negative |
| ATA | 35 | −0.11 | 0.03252 | negative |
| AAA | 36 | −0.1 | 0.03 | negative |
| GGAG | 37 | −0.11 | 0.0532 | negative |
| CTG | 38 | −0.09 | 0.0034 | negative |

Example 4

Creation of Logistic Regression Model and Reducing the Complexity of the Model Through Likelihood-Ratio Test The logistic regression model relates the probability of activity with the motif content of each oligonucleotide. After model creation, the likelihood ratio test was used as a selection procedure that reduces complexity of the model by removing motifs that are less significant for the quality of prediction. Ten motifs (five positive and five negative predictors) remained in the list as being most significant for the model; these are shown in Table 3. These motifs were further verified in additional testing that involved a database of 908 oligonucleotides (set 3), which includes unpublished data from Isis Pharmaceuticals Inc. Nine of these ten motifs, (CCGG being the exception), were confirmed to be predictors of oligonucleotide activity in the set 3 database. There is a consistent effect of the presence of one or more of the positive predictor motifs on the proportion of active antisense oligonucleotides. Interestingly, all of the motifs with positive correlation coefficients in Table 3 are C-rich.

TABLE 3

Oligonucleotide motifs whose presence is predictive of antisense oligonucleotide activity

| Motif | SEQ ID NO: | Correlation coefficient | Statistical Significance | Effect[1] |
|---|---|---|---|---|
| CCAC | 1 | 0.3 | $2.6 \times 10^{-09}$ | positive |
| TCCC | 4 | 0.3 | $1.5 \times 10^{-08}$ | positive |
| ACTC | 8 | 0.2 | $4.7 \times 10^{-05}$ | positive |
| GCCA | 11 | 0.2 | 0.0015 | positive |
| CTCT | 20 | 0.1 | 0.007 | positive |
| GGGG | 21 | −0.2 | $4.7 \times 10^{-06}$ | negative |
| ACTG | 26 | −0.2 | 0.0006 | negative |
| TAA | 23 | −0.2 | 0.002 | negative |
| CCGG | 34 | −0.1 | 0.02 | negative |
| AAA | 36 | −0.1 | 0.03 | negative |

[1]The presence of motifs whose effect is shown as "positive" positively correlates with antisense activity. Conversely, the presence of motifs whose effect is shown as "negative" negatively correlates with antisense activity.

Together, these findings demonstrate that antisense oligonucleotides containing one or more activity-enhancing motifs (preferably including but not limited to those in Table 1, and more preferably those identified as positive in Table 3) are more likely to be active than antisense oligonucleotides lacking such positive motifs. Antisense oligonucleotides containing one or more activity-decreasing motifs (including but not limited to those in Table 2) are less likely to be active than antisense oligonucleotides lacking such negative motifs. Thus it is desired to choose antisense oligonucleotide target sequences which contain one or more motifs which are complementary to the activity-enhancing oligonucleotide motifs, and to avoid target sequences which contain one or more motifs which are complementary to the activity-decreasing oligonucleotide motifs. Most preferred are antisense target sequences which contain one or more motifs which are complementary to the positive predictor sequences shown in Table 3 as "positive". It is preferable to exclude target sequences which contain one or more motifs complementary to the negative predictor sequences shown as "negative" in Table 3. Based on the oligonucleotide motifs shown in Table 1, the following target motifs (shown in Table 4 along with their complementary oligonucleotide motifs) are desired to be included in the sequence region to be targeted for antisense inhibition.

TABLE 4

Activity-enhancing target sequence motifs

| Antisense Motif sequence 5'_3' | SEQ ID NO: | Target Motif sequence 5'_3' | SEQ ID NO: | Direction of effect |
|---|---|---|---|---|
| CCAC | 1 | GTGG | 39 | positive |
| CCA | 2 | TGG | 40 | positive |
| CCC | 3 | GGG | 22 | positive |
| TCCC | 4 | GGGA | 41 | positive |
| CCCA | 5 | TGGG | 28 | positive |
| CCCT | 6 | AGGG | 42 | positive |
| CCCC | 7 | GGGG | 21 | positive |
| ACTC | 8 | GAGT | 43 | positive |
| ATCC | 9 | GGAT | 44 | positive |
| CACC | 10 | GGTG | 45 | positive |
| GCCA | 11 | TGGC | 46 | positive |
| ATC | 12 | GAT | 47 | positive |
| CAC | 13 | GTG | 48 | positive |
| CTC | 14 | GAG | 49 | positive |
| GCAT | 15 | ATGC | 50 | positive |
| ACCA | 16 | TGGT | 51 | positive |
| CATC | 17 | GATG | 52 | positive |
| TCC | 18 | GGA | 30 | positive |
| ACC | 19 | GGT | 53 | positive |
| CTCT | 20 | AGAG | 54 | positive |

Figure 3:
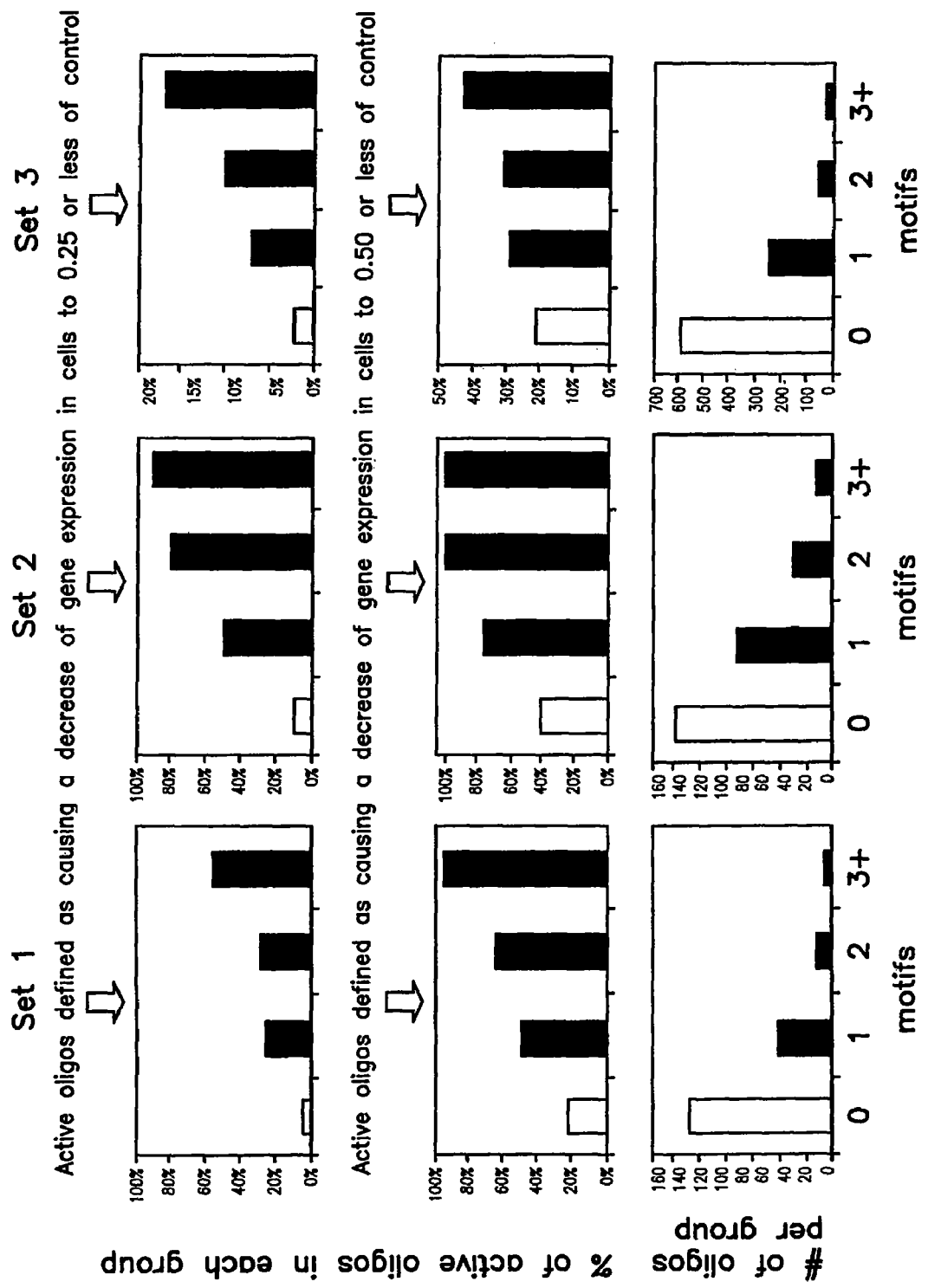
FIG. 3 is a series of bar graphs showing a correlation of antisense oligonucleotide activity with the presence of varying numbers of positive sequence motifs (CCAC, TCCC, ACTC, GCCA, CTCT (SEQ ID NO: 1, 4, 8, 11 and 20). The black bars represent groups of oligonucleotides with 1, 2, or 3+ motifs that are positively correlated with activity. The white bars represent groups of oligonucleotides without positive motifs (may contain negative motifs). Sets 1, 2 and 3 are described hereinbelow. The top row of graph panels shows active oligonucleotides, defined as causing at least 75% reduction in target protein or mRNA expression. The middle row of graph panels shows active oligonucleotides, defined as causing at least 50% reduction in target protein or mRNA expression. The bottom row of graph panels shows the number of oligonucleotides per group.

As shown in FIG. 3, the proportion of active molecules is higher for the group of oligonucleotides with multiple activity-enhancing motifs in comparison with the group of oligonucleotides with only one positive motif. Thus it is highly preferred to select antisense target sequence regions which contain two or more sequence motifs complementary to activity-enhancing (positive) oligonucleotide motifs is highly preferred.

Based on the above results it is also desired to choose antisense oligonucleotide target sequence regions which do not contain motifs which are complementary to the activity-decreasing oligonucleotide motifs. Based on the oligonucleotide motifs shown in Table 2, the following target motifs (shown in Table 5 along with their complementary oligonucleotide motifs) are desired to be avoided in the sequence region to be targeted for antisense inhibition.

TABLE 5

Activity-decreasing target sequence motifs

| Antisense Motif sequence 5'_3' | SEQ ID NO: | Target Motif sequence 5'_3' | SEQ ID NO: | Direction of effect |
|---|---|---|---|---|
| GGGG | 21 | CCCC | 7 | negative |
| GGG | 22 | CCC | 3 | negative |
| GGCT | 24 | AGCC | 55 | negative |
| TAAA | 25 | TTTA | 56 | negative |
| ACTG | 26 | CAGT | 57 | negative |
| GAAA | 27 | TTTC | 58 | negative |
| TGGG | 28 | CCCA | 5 | negative |
| AAAT | 29 | ATTT | 59 | negative |
| GGA | 30 | TCC | 18 | negative |
| CTGG | 31 | CCAG | 60 | negative |
| ATAA | 32 | TTAT | 61 | negative |
| AATA | 33 | TATT | 62 | negative |
| CCGG | 34 | CCGG | 34 | negative |
| ATA | 35 | TAT | 63 | negative |
| GGAG | 37 | CTCC | 64 | negative |
| CTG | 38 | CAG | 65 | negative |

Example 5

Software for Motif and Database Analysis

For the database analysis, the program Oligostat (Tsodikov, A. et al., Dept. of Oncological Sciences, University of Utah; program available upon request) was created and used in combination with Excel (Microsoft, Inc., Redmond Wash.). This program facilitates the performance of a series of standard statistical analyses as follows: Oligostat first calculates the correlation coefficients (T-test; Sheskin, D. J., Handbook of Parametric and Nonparametric Statistical Procedures, CRC Press, Boca Raton, Fla., 1997) of oligonucleotide activity and motif occurrence with motif length varying from three to four nucleotides. Then, using motifs with significant correlation coefficient values, Oligostat allows the user to create a logistic regression model (Sheskin, ibid.) that relates the probability of activity with the motif content of each oligonucleotide. After this Oligostat allows the user to perform a likelihood ratio test (Sheskin, ibid.) for the selection of motifs that are most significant for the model.

What is claimed is:

1. A method of preparing an antisense compound comprising:
    generating a set of candidate antisense sequences wherein each candidate antisense sequence consists of 12 to 25 nucleobases and is complementary to a preselected target nucleic acid sequence;
    eliminating from the set of candidate antisense sequences any candidate antisense sequence comprising at least one motif from a set of negative prediction motifs, wherein the set of negative prediction motifs comprises at least one-negative prediction sequence motif selected from: GGGG, ACTG, TAAA, CCGG, and AAA;
    selecting at least one test sequence from the set of remaining candidate antisense sequences; and
    synthesizing at least one oligonucleotide having one of the at least one test sequences and testing the oligonucleotide for its ability to inhibit expression of the preselected target nucleic acid.

2. The method of claim 1, wherein the set of negative prediction motifs comprises at least two negative prediction sequence motifs selected from: GGGG, ACTG, TAAA, CCGG, and AAA.

3. The method of claim 1, wherein the set of negative prediction motifs comprises at least three negative prediction sequence motifs selected from: GGGG, ACTG, TAAA, CCGG, and AAA.

4. The method of claim 1, wherein the set of negative prediction motifs comprises at least four negative prediction sequence motifs selected from: GGGG, ACTG, TAAA, CCGG, and AAA.

5. The method of claim 1, wherein the set of negative prediction motifs comprises the negative prediction sequence motifs: GGGG, ACTG, TAAA, CCGG, and AAA.

* * * * *